United States Patent
Hellgren et al.

(10) Patent No.: US 10,866,225 B2
(45) Date of Patent: Dec. 15, 2020

(54) WIDE RANGE GAS DETECTION USING AN INFRARED GAS DETECTOR

(71) Applicant: INFICON Holding AG, Bad Ragaz (CH)

(72) Inventors: Johan Hellgren, Linkoping (SE); Fredrik Enquist, Linkoping (SE); Henrik Vennerberg, Linkoping (SE)

(73) Assignee: INFICON Holding AG, Bad Ragaz (CH)

( * ) Notice: Subject to any disclaimer, the term of this patent is extended or adjusted under 35 U.S.C. 154(b) by 185 days.

(21) Appl. No.: 16/069,690

(22) PCT Filed: Jan. 6, 2017

(86) PCT No.: PCT/EP2017/050268
§ 371 (c)(1),
(2) Date: Jul. 12, 2018

(87) PCT Pub. No.: WO2017/121688
PCT Pub. Date: Jul. 20, 2017

(65) Prior Publication Data
US 2019/0011414 A1    Jan. 10, 2019

(30) Foreign Application Priority Data

Jan. 13, 2016   (EP) .................................... 16151030

(51) Int. Cl.
*G01N 33/00*     (2006.01)
*G01N 21/3504*   (2014.01)
*G01N 21/27*     (2006.01)

(52) U.S. Cl.
CPC ....... *G01N 33/0026* (2013.01); *G01N 21/276* (2013.01); *G01N 21/3504* (2013.01)

(58) Field of Classification Search
CPC ............. G01N 21/276; G01N 33/0026; G01N 21/3504
See application file for complete search history.

(56) References Cited

U.S. PATENT DOCUMENTS

| | | | |
|---|---|---|---|
| 4,755,675 A | 7/1988 | Rosenfeld et al. | |
| 5,572,032 A | 11/1996 | Fujiwara et al. | |
| 6,484,563 B1 * | 11/2002 | Enquist ............. | G01N 33/0026 324/71.5 |
| 7,030,381 B2 | 4/2006 | Kilian et al. | |
| 2003/0000285 A1 | 1/2003 | Enquist et al. | |
| 2014/0361173 A1 | 12/2014 | Kuester et al. | |

FOREIGN PATENT DOCUMENTS

| | | |
|---|---|---|
| EP | 3163290 A1 | 5/2017 |
| EP | 3163299 A1 | 5/2017 |
| JP | H07159323 A | 6/1995 |
| JP | 2004205272 A | 7/2004 |

* cited by examiner

*Primary Examiner* — Justin N Olamit
(74) *Attorney, Agent, or Firm* — The Webb Law Firm

(57) ABSTRACT

Method for wide range gas detection using a gas detection system comprising a sample gas inlet, a reference gas inlet, a gas modulation valve and a gas analyzer, wherein the gas modulation valve alternatingly connects the sample gas inlet to the gas analyzer during a sample gas time period and the reference gas inlet to the gas analyzer during a reference gas time period, characterized in that the sample gas time period is shorter than the reference gas time period such that the sample gas concentration in the gas analyzer is reduced.

9 Claims, 2 Drawing Sheets

WIDE RANGE GAS DETECTION USING AN INFRARED GAS DETECTOR

CROSS-REFERENCE TO RELATED APPLICATIONS

This application is the United States national phase of International Application No. PCT/EP2017/050268 filed Jan. 6, 2017, and claims priority to European Patent Application No. 16151030.0 filed Jan. 13, 2016, the disclosures of which are hereby incorporated in their entirety by reference.

BACKGROUND OF THE INVENTION

Field of the Invention

The invention refers to a wide range gas detection method for detecting both low and high concentrations of a target gas in a gas sample using a gas analyzer and a gas modulation valve which alternatingly connects a reference gas inlet and a sample gas inlet to the gas analyzer.

Description of Related Art

Such a gas modulation valve and a respective gas modulation method is described in U.S. Pat. No. 7,030,381 B2, the contents of which are incorporated herein by reference. Gas detectors according to U.S. Pat. No. 7,030,381 B2 may comprise a sample gas inlet through which the gas to be detected (target gas) is sucked in and a reference gas inlet through which gas from the surrounding atmosphere is sucked in as a reference gas. The gas modulation valve connects the sample gas inlet and the reference gas inlet to the inlet of a gas sensor, such as an infrared gas sensor. The infrared gas sensor may, for example, have a cuvette comprising the inlet and a respective outlet for the gas to be analyzed, an infrared light source and an infrared detector. The gas flow path from the gas modulation valve to the inlet of the gas sensor is alternately connected to the sample gas inlet and to the reference gas inlet by the gas modulation valve. The switching by the gas modulation valve between the sample gas inlet and the reference gas inlet preferably occurs in a periodical manner at a periodic frequency, as described in U.S. Pat. No. 7,030,381 B2.

A gas detection method employing gas modulation using a gas modulation valve switching between a reference gas inlet and a sample gas inlet is also described in European Patent Application No. 15192115.2, the contents of which are incorporated herein by reference.

The main purpose of U.S. Pat. No. 7,030,381 B2 is to filter out or compensate for an increased level of the target gas in the ambient atmosphere surrounding the gas detector by presenting an output signal representing the difference in concentration of target gas at the sampling point and in the ambient atmosphere. Another consequence of using the gas modulation is a strongly enhanced signal-to-noise ratio as the gas modulation modulates the actual parameter to analyze, namely the gas concentration. The signal is the difference between light transmitted through the gas and through the reference instead of an absolute value of light intensity. Analyzing the detector signal at the gas modulation frequency strongly suppresses various noise signals with other frequencies.

Infrared gas analyzers detect infrared radiation passing through a gas sample. Typically, an IR gas analyzer comprises an infrared source, a measurement section, such as a cuvette having a gas inlet, and a gas outlet and an infrared sensor. The infrared source emits IR radiation into and through the measurement section where it passes through the gas sample contained therein. The infrared sensor receives and senses the IR radiation passing through the gas sample. A typical infrared sensor often used in this type of detector is a non-dispersive infrared absorption detector (NDIR sensor). NDIR sensors measure the amount of infrared radiation in one or several wavelength ranges in the radiation passed through the gas to be analyzed. The selectivity of an NDIR sensor is determined by selecting the appropriate wavelength ranges to fit specific absorption lines of the respective gas to be measured. The measurement principle is based on the fact that specific gas components absorb infrared radiation of specific wavelengths. The absorption ranges are to be detected by the infrared gas analyzer.

The infrared sensor transduces the magnitude of variations in incoming IR radiation energy into an electrical signal. Some IR sensors employ piezo materials and are known as pyroelectric sensors. The piezo material absorbs incoming radiation causing a temperature shift which in turn induces a temporary electrical potential across the material that can be used as a measurement of the change in incoming radiation intensity.

Detection of low target gas concentrations in a gas sample in the range of parts per million (ppm) requires a long optical path, i.e. a long path in which the infrared radiation can interact with the molecules in the gas. Using affordable radiation sources, optical filters and infrared radiation detectors typically results in optical path length in the order of 50-150 mm to achieve a sensitivity of 1-10 ppm for methane. An optical path longer than 150 mm typically does not, significantly, increase the performance further due to reflection losses in the gas tube carrying the gas and forming the cuvette of the infrared gas detector.

The reason for "long optical paths" to be used in the gas detector is to get a signal variation between clean air and the low concentration sample that is significantly larger than the noise in the system. Noise sources are mainly on the detector side including the detector itself and circuitry used to amplify and convert the signal to a manageable digital or analog signal.

The absorption in the gas follows Beer's Law which can be written as follows for the light intensity transmitted through an optical path (assuming non-divergent light):

$$I = I_0 \times e^{\varepsilon L c}$$

Where:
I=Intensity of light after passing through length L of gas sample.
$I_0$=Intensity of light passing entering gas sample optical path.
ε=Molar absorptivity (depending on gas type)
L=Length of optical path.
c=Concentration of gas absorbing the light.

This means that for a given length Δx there will be a fixed relative attenuation of the signal. This effect is illustrated in FIG. 1.

As can be seen the differential sensitivity decreases with concentration and length of the optical path. The optical path needs to be long to be optimized for low ppm sensitivity and it therefore becomes very difficult to see the difference between for example 90% and 95% of the target gas.

An optical path being so long that this "saturation" phenomenon occurs is referred to as a "long optical path". In atmosphere content measurements it is referred to as a "thick atmosphere".

This phenomenon makes it difficult to combine low and high concentration analysis in one and the same cuvette.

A saturation phenomenon also occurs on many other types of sensors, in particular, chemical and electrochemical sensors. The reason for the saturation phenomenon might be different for other types of sensors as compared to infrared gas analyzers.

SUMMARY OF THE INVENTION

It is an object of the invention to improve the capability of a low concentration optimized gas analyzer using gas modulation to also analyze high gas concentrations.

The subject matter of the invention is described in non-limiting embodiments or aspects below, and the invention is applicable to other sensor types, such as chemical gas analyzers or electrochemical gas analyzers, in addition to infrared gas analyzers.

Accordingly, the sample gas time period during which the gas modulation valve connects the sample gas inlet to the gas analyzer is shorter than the reference gas time period during which the gas modulation valve connects the reference gas inlet to the gas analyzer. The alternating switching of the gas modulation valve between the reference gas inlet and the sample gas inlet results in a gas modulation at a gas modulation frequency. The shorter the sample gas time period compared to the reference gas time period, the lower is the sample gas concentration and, thus, the concentration of possible target gas within the gas analyzer. The longer the sample gas time period compared to the reference gas time period, the larger is the amount of sample gas and, thus, possible target gas within the gas analyzer. The ratio between the length of the sample gas time period and the total gas modulation period is called duty cycle. The duty cycle hence determines the amount of sample gas in the cuvette (measurement volume of the infrared gas analyzer).

The method of the invention can be employed for different types of gas analyzers which are optimized for low gas concentrations, in order to improve the capability of the gas analyzer to also analyze high gas concentrations. This is particularly advantageous for gas analyzers which are subject to a saturation phenomenon where there is no linearity between the concentration of sample gas/target gas and the measurement signal of the gas analyzer. This saturation phenomenon occurs with infrared gas analyzers as well as with different types of chemical gas analyzers, such as electrochemical gas analyzers.

The response of the gas sensor within the gas analyzer should be adapted to the cycle time of the gas modulation valve. The sensor should not be too fast in order to avoid saturation in a single sample gas pulse. By avoiding saturation it is possible to get a more accurate reading from the gas sensor by calculating the time weighted average of the signal over one or a number of gas modulation cycles.

Saturation could also mean that the devices and/or algorithms used to evaluate the sensor signal are saturating. This can be an amplifier or an analog to digital converter going out of range. This type of saturation can also be avoided by the present invention.

An infrared gas analyzer preferably comprises an infrared source (infrared lamp), an absorption cuvette having a gas inlet connected to the gas modulation valve and a gas outlet, wherein the infrared sensor detects infrared radiation generated by the infrared source and passing through the absorption cuvette. The infrared sensor thus detects infrared radiation generated by the infrared source and passing through the sample gas and possible target gas within the absorption cuvette.

The gas flow through or across the infrared gas analyzer is preferably generated by a pump. The pump may be located within the gas flow path connecting the gas modulation valve and the infrared gas analyzer.

The gas modulation frequency and the gas flow through the infrared gas analyzer generated by the pump are chosen such that at least one entire and, preferably, more than five sample gas pulses are present in the gas analyzer (cuvette) at any given time during the gas analysis.

The measurement signal generated by the gas analyzer is analyzed at a detection frequency which may correspond to the gas modulation frequency or which may be an integer multiple of the gas modulation frequency. In addition, the measurement signal may simultaneously also be analyzed at an additional frequency or at several additional frequencies each being integer multiples of the gas modulation frequency.

The infrared source is switched on and off repeatedly at a lamp modulation frequency which may preferably be lower than the gas modulation frequency. The measurement signal of the infrared gas analyzer may then be analyzed at a detection frequency corresponding to the lamp modulation frequency or being an integer multiple of the lamp modulation frequency. The measurement signal of the infrared gas analyzer may simultaneously also be analyzed at one or several other frequencies each being integer multiples of the lamp modulation frequency.

The gas modulation frequency should be an integer multiple of the lamp modulation frequency. In the above, an integer multiple may be the same frequency, twice the frequency, three times the frequency, and so on.

The obvious solution for this problem would be to use a second shorter path for detecting high concentrations. This would involve extra costs for an extra cuvette and an extra detector. Another possibility would be to place an extra detector in the beginning of the long cuvette, thus forming a second short path. The latter solution would save the cost for a second cuvette but would have a negative impact on the signal by causing stray losses due to diverted light in the opening to the second detector.

The invention instead uses the gas modulation valve to create a virtual short path by adjusting the duty cycle of the valve so that only part of the cuvette is filled with sample containing the target gas.

In normal high sensitivity mode (for detecting low concentrations) the gas modulation valve is typically switched with a 50% duty cycle (50% sample and 50% reference) for best performance. Furthermore, the pump speed is selected to fill the entire cuvette with sample gas and air, respectively, in a time shorter than each of the two sampling phases.

$$\Phi_{pump} > \frac{V_{cuvette}}{0.5 \times \frac{1}{f_{Valve}}}$$

Where:
$\phi_{pump}$=Average pump flow
$V_{cuvette}$=Internal volume of cuvette
$f_{valve}$=Gas modulation frequency Making the flow too large has no or little impact on the signal but will waste energy and consume sample. Making the flow just high enough for filling the cuvette twice in a full modulation period it is possible to "dilute" the sample by using a sampling time that is shorter than the reference time as shown below. Another way of looking at the situation in the cuvette is that the optical path is made shorter. The length that the light passes through the gas sample is the same as the length of the gas sample and hence shorter than the full cuvette length. The cuvette is made virtually shorter.

The duty cycle variation method can be difficult to employ together with membrane pumps typically used in portable gas detector equipment. There are two reasons for this. First, the flow is not very stable over time due to wear and particle contamination and can, therefore, not be adequately predicted or controlled by voltage regulation or even tachometer control. Secondly, the flow from the pump varies greatly at different phases of the pumping cycle. The pump is typically delivering flow only during a period of less than 50% of each revolution or pumping cycle.

This uncertainty in flow creates variations in the average gas concentration in the cuvette when using duty cycle dilution. This is because it cannot be precisely controlled that a new gas pulse starts entering the column when the previous pulse starts leaving the column. Small variations in pump speed can therefore generate large errors. Basically, the error will be as large as the variation in the pump flow causing calibration drift as well as poor accuracy.

One way of reducing this phenomenon is to use a higher gas modulation frequency with the same duty cycle and thereby creating a large number of short gas pulses in the cuvette. In this case, the error will be limited to the variation in number of pulses divided with the average number of pulses in the cuvette. For example, by choosing a modulation frequency that is roughly $$f_{valve} \approx 10 \times \frac{\Phi_{pump}}{V_{cuvette}}$$

this error can be limited to 1/n where n is the average number of pulses in the cuvette and flow variation is less than 1/n. In the example, this corresponds to 1/10=10% for up to +/−10% variation in pump flow.

While an infrared gas analyzer typically comprises a cuvette through which the gas sample passes, other types of gas analyzers, such as chemical or electrochemical gas analyzers, are constructed such that the gas to be analyzed passes across or past a sensor (chemical or electrochemical sensor). If reference gas pulses are introduced in between the sample gas pulses by respective switching of the gas modulation valve, an average gas concentration can be achieved which is lower than in the sample gas itself. While the gas concentration in the gas sample may be in saturation, the lower average gas concentration may be below saturation where a linearity between the measurement signal intensity and the gas concentration prevails. This allows gas detection over a wide extended range of gas concentrations.

If the valve modulation time (valve modulation frequency) is faster than the response time of the gas sensor, the gas sensor can be prevented from going into saturation at any given time and the diluted average gas concentration can be evaluated as the average of the measurement signal.

BRIEF DESCRIPTION OF THE DRAWINGS

In the following, examples of the invention are discussed with reference to FIGS. 1-4. In particular.

DESCRIPTION OF THE INVENTION

Figure 2:
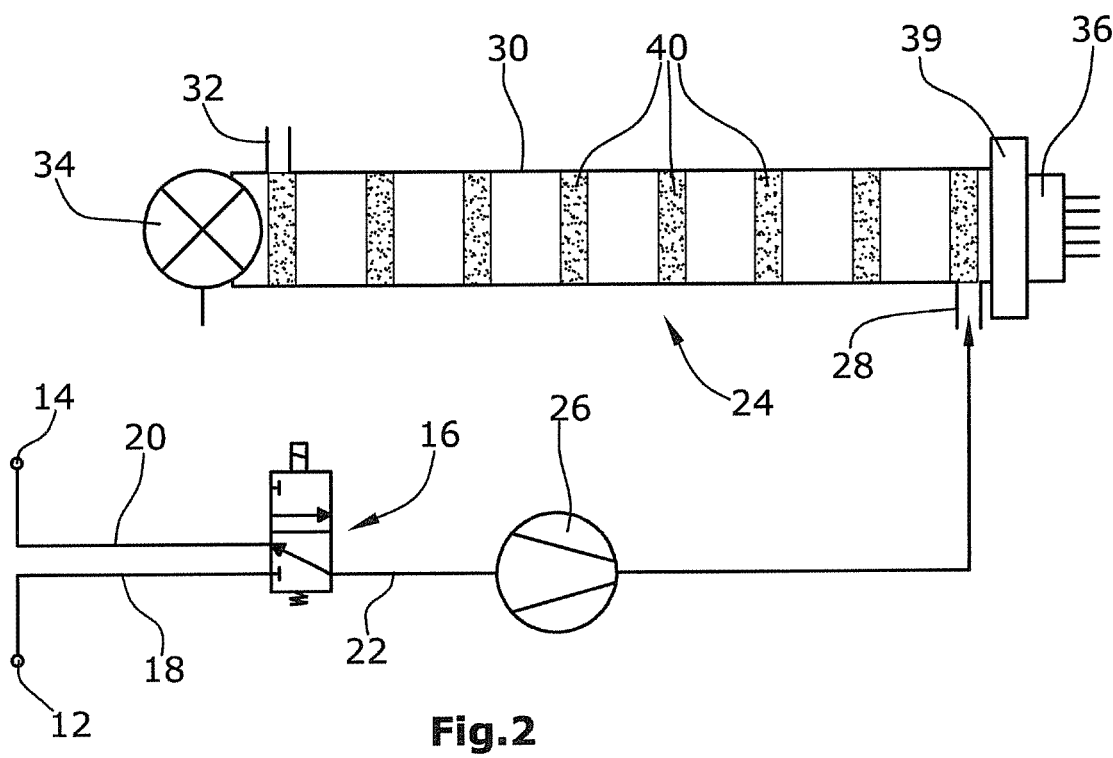
FIG. 2 shows a schematic illustration of a first embodiment.
Figure 3:
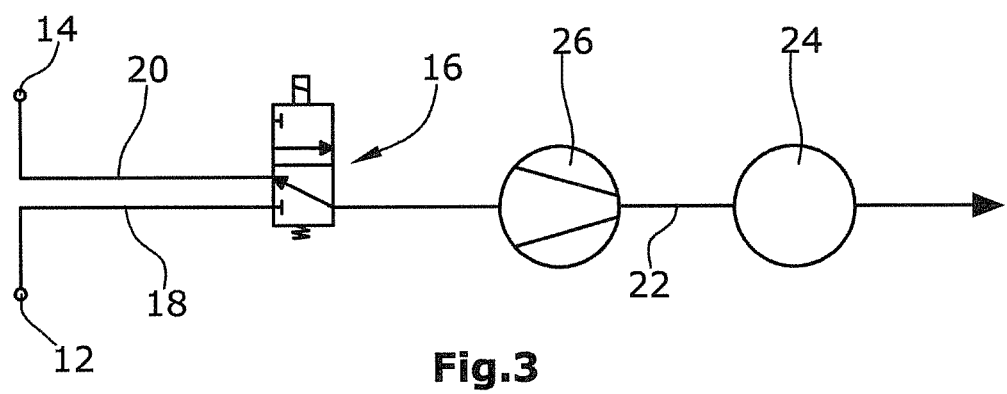
FIG. 3 shows a schematic illustration of a second embodiment.
Figure 4:
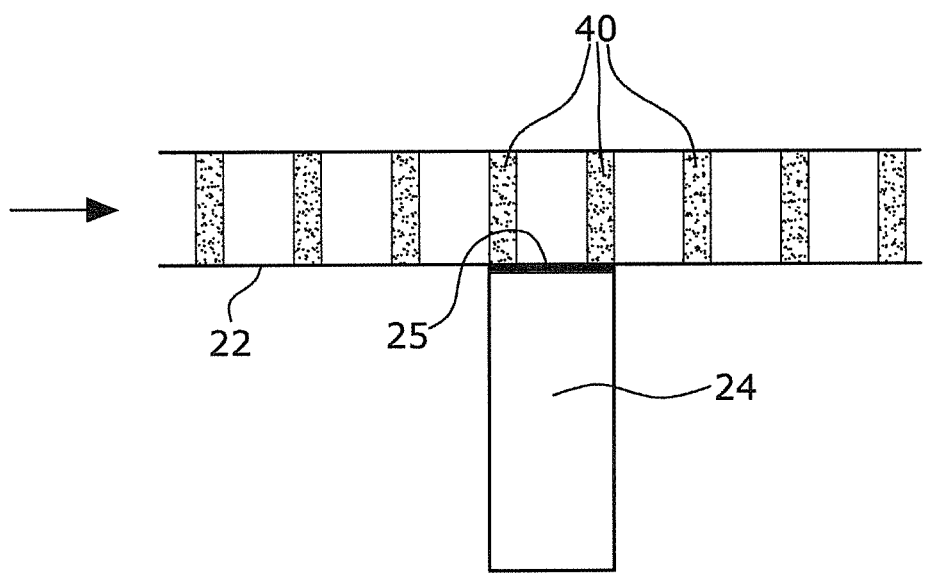
FIG. 4 shows a detail of the embodiment according to FIG. 3.

With reference to FIGS. 2-4, depicted are a sample gas inlet 12 and a reference gas inlet 14 are connected to a gas modulation valve 16 via respective sample and reference gas conduits 18, 20. The gas modulation valve 16 alternatingly connects the sample gas conduit 18 and the reference gas conduit 20 to the gas flow path 22 connecting the gas modulation valve 16 and the gas analyzer 24. The gas analyzer 24 of the first embodiment according to FIG. 2 is a non-dispersive infrared (NDIR) sensor comprising an absorption cuvette 30. The gas analyzer 24 of the second embodiment according to FIGS. 3 and 4 is an electrochemical gas analyzer employing an electrochemical gas sensor. The gas flow path 22 contains a sample vacuum pump 26 located between the gas modulation valve 16 and the gas analyzer 24. The sample gas inlet 12 and the reference gas inlet 14 may be part of a handheld gas detector probe. This concept is described in U.S. Pat. No. 7,030,381 B2 and in European Patent Application Nos. 15192135.0 and 15192115.2, the contents of which are incorporated herein by reference.

Accordingly, the gas modulation valve 16 switches between the reference gas conduit 18 originating from the reference gas inlet 12 and the sample gas conduit 20 originating from the sample gas inlet 12. The gas modulation valve 16 connects either of the conduits 18, 20 with the gas flow path (main gas conduit) 22. The gas to be analyzed is conveyed through the gas flow path 22 to the gas analyzer 24.

The absorption cuvette 30 of the gas analyzer 24 of FIG. 2 comprises an inlet 28 through which the gas which is pumped by the sample pump 26 is guided into the absorption cuvette 30. The gas exits the cuvette through an outlet 32. An infrared source 34 is located at one end of the cuvette 30. The infrared source 34 is separated from the volume of the cuvette 30 through which the gas passes by an optical window which is not shown in the figures. At the opposite end of the cuvette 30, an optical filter 39 and an infrared sensor 36 are located and separated from the volume of the cuvette 30 through which the gas sample passes by a further optical window which is not shown in the figures. The optical windows may be made of Si, Ge or $CaF_2$ and are transparent for the infrared radiation originating from the source 34. The windows thereby separate the infrared source 34, the sensor 36 and the optical filter 39 from the gas flow path through the cuvette 30.

The optical filter 39 is preferably a dichroic or interference filter restricting the wavelength range passing through the optical window and detected by the infrared sensor 36, to the characteristic wavelength of the gas to be detected (target gas), for example methane. In general, the filter 39 should restrict the wavelength range of the infrared radiation to a wavelength range comprising absorbing wavelengths of the target gas while not comprising any absorbing wavelengths of other characteristic gases.

Infrared radiation originating from the infrared source 34 radiates through the optical window not shown in the figures into the volume of the cuvette 30 and through the gas sample passing through the cuvette 30, and then through the further optical window not shown in the figures and the optical filter 39 before being received by the infrared sensor 36.

The gas modulation valve 16 is used to create a signal modulation for noise reduction and signal amplification. Thereby, the valve 16 takes gas from the sample gas inlet 12 at the actual point of interest, or from the reference gas inlet 14 from the background air in an alternating cycle. The output signal of the gas analyzer 24 is analyzed in relation to the switching frequency of the modulation valve 16 (gas modulation frequency) and sometimes also in relation to the phase in order to improve the sensitivity and to reduce background noise.

Figure 1:
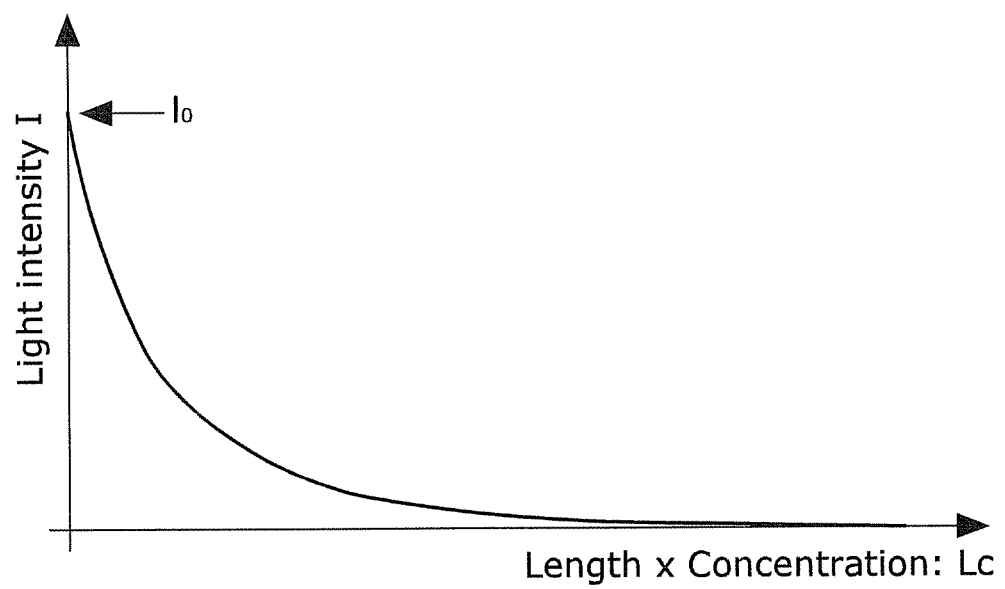
FIG. 1 shows a plot illustrating the saturation phenomenon.

A control device not shown in the figures controls the switching of the gas modulation valve 16 and the gas modulation frequency. When analyzing high concentrations the switching is controlled such that the sample gas time period during which the sample gas inlet 12 is connected to the infrared analyzer 24 is shorter than the reference gas time period during which the reference gas inlet 14 is connected to the gas analyzer 24. Thereby, short sample gas pulses 40 are generated in the cuvette 30. The cuvette 30 is filled with reference gas originating from the reference gas inlet 14 between adjacent sample gas pulses 40. This results in a reduced concentration of sample gas within the cuvette 30 and allows analyzing also high target gas concentrations in the cuvette 30. The cuvette 30 is long enough, i.e. the distance between the two optical windows is large enough, to also analyze low target gas concentrations in the range of 1-10 ppm. The path length (distance between the two optical windows) is in the order of 50 mm-150 mm where it would typically be difficult to analyze large concentrations of a thick atmosphere due to the saturation phenomenon described above with regard to FIG. 1.

The gas analyzer 24 generates an electronic detector signal that is analyzed by an evaluation device that is not shown in the pictures. The evaluation device evaluating the measurement signal from the gas analyzer 24 and the control device controlling the gas modulation valve 16 may be a single component sharing a single processor or separate components which might be electronically connected with each other to share and exchange data.

The evaluation device analyzes and evaluates the measurement signal from the sensor 36 at a detection frequency which might be controlled by the control device. The detection frequency is controlled by the control device depending on the gas modulation frequency. The detection frequency should be an integer multiple (once, twice, three times, . . . ) of the gas modulation frequency. At the detection frequency, the evaluation device captures the measurement signal from the sensor 36 in order to perform the gas analysis.

The control device also controls the lamp modulation frequency at which the power to the infrared source 34 is modulated. The lamp modulation frequency should be lower than the gas modulation frequency of the switching valve 16 while the detection frequency corresponds to the lamp modulation frequency. This means that the electronic measurement signal from the sensor 36 is analyzed by the evaluation device at the lamp modulation frequency. The gas modulation frequency is an integer multiple of (once, twice, etc.) the lamp modulation frequency.

FIGS. 3 and 4 show an alternative embodiment employing an electrochemical gas analyzer 24. In contrast to the first embodiment, where the gas sample is guided through the infrared gas analyzer, the gas sample of the second embodiment is guided past or across the measurement surface 25 of the electrochemical gas analyzer 24. The gas to be analyzed thus contacts the measurement surface 25 such that an electrochemical reaction occurs which generates an electronic measurement signal. The measurement signal is analyzed at a detection frequency being an integer multiple of the gas modulation frequency, at which the gas modulation valve 16 switches between the sample gas inlet 12 and the reference gas inlet 14.

The sample vacuum pump 26 could, in both embodiments, alternatively be placed downstream of the gas analyzer 24, i.e. behind the outlet 32. The advantage of locating the pump 26 within the main gas conduit 22 between the gas inlet 12 and the gas analyzer 24 is that pressure drops in the cuvette 30 due to varying restrictions in sampling probes are avoided.

Moreover, it is a general idea of the invention to switch the gas modulation valve 16 in a way which does not provide 50% of the sample gas from the sample gas inlet 12 and 50% of the reference gas from the reference gas inlet 14 to the gas analyzer 24, but rather a lower amount of the sample gas compared to the reference gas. This is controlled by the control device controlling the sample gas time period and the reference gas time period.

During the sample gas time period, the sample gas inlet 12 is connected to the gas analyzer 24 and during the reference gas time period, the reference gas inlet 14 is connected to the gas analyzer 24 by the gas modulation valve 16. The control device controls the switching of the gas modulation valve 16 such that the sample gas time period is lower than the reference gas time period, preferably five times lower and more preferably around ten times lower. In other words, the ratio of the sample gas time period and the reference gas time period should be lower than 1 and preferably 1:5 and more preferably around 1:10.

The invention claimed is:

1. A method for wide range gas detection using a gas detection system comprising a sample gas inlet, a reference gas inlet, a gas modulation valve, and a gas analyzer, the method comprising alternatingly connecting, using the gas modulation valve, the sample gas inlet to the gas analyzer during a sample gas time period and the reference gas inlet to the gas analyzer during a reference gas time period,
   wherein the sample gas time period is shorter than the reference gas time period such that a concentration of sample gas in the gas analyzer is reduced, and
   wherein the gas analyzer is an infrared absorption gas analyzer comprising an infrared source for generating infrared radiation radiating through the sample gas, and an infrared detector for detecting the infrared radiation.

2. The method according to claim 1, wherein a number of gas pulses in the gas analyzer generated by switching between the sample gas inlet and the reference gas inlet, by alternatingly connecting using the gas modulation valve, is larger than 1 during gas analysis.

3. The method according to claim 2, wherein the number of gas pulses is more than 5.

4. The method according to claim 1, further comprising analyzing a measurement signal of the gas analyzer at a detection frequency being an integer multiple of a gas modulation frequency at which the gas modulation valve switches between the sample gas inlet and the reference gas inlet.

5. The method according to claim 4, wherein the measurement signal generated by the gas analyzer is additionally analyzed at an additional frequency or at several additional frequencies each being integer multiples of the gas modulation frequency.

6. The method according to claim 1, wherein a power of the infrared source of the gas analyzer is modulated at a lamp modulation frequency that is lower than a gas modulation frequency at which the gas modulation valve switches between the sample gas inlet and the reference gas inlet, the method further comprising analyzing a measurement signal of the gas analyzer at an integer multiple of the lamp modulation frequency.

7. The method according to claim 6, wherein the measurement signal of the gas analyzer is additionally analyzed at an additional frequency or several additional frequencies each being integer multiples of the lamp modulation frequency.

8. The method according to claim 6, wherein the gas modulation frequency is an integer multiple of the lamp modulation frequency.

9. The method according to claim 6, wherein gas modulation and lamp modulation are performed in combination.

\* \* \* \* \*